US009242101B2

(12) United States Patent
Ip et al.

(10) Patent No.: US 9,242,101 B2
(45) Date of Patent: Jan. 26, 2016

(54) METHOD, DEVICE AND PROGRAM TO DIFFERENTIATE PACEMAKER-MEDIATED TACHYCARDIA (PMT) FROM TRACKING OF SINUS OR ATRIAL TACHYCARDIA (AT)

(75) Inventors: James E. Ip, New York, NY (US); Bruce B. Lerman, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 18 days.

(21) Appl. No.: 13/994,525

(22) PCT Filed: Dec. 14, 2011

(86) PCT No.: PCT/US2011/064970
§ 371 (c)(1),
(2), (4) Date: Jul. 29, 2013

(87) PCT Pub. No.: WO2012/082937
PCT Pub. Date: Jun. 21, 2012

(65) Prior Publication Data
US 2013/0303925 A1     Nov. 14, 2013

Related U.S. Application Data

(60) Provisional application No. 61/422,779, filed on Dec. 14, 2010.

(51) Int. Cl.
*A61N 1/37*     (2006.01)
*A61N 1/375*    (2006.01)
(Continued)

(52) U.S. Cl.
CPC ............ *A61N 1/3702* (2013.01); *A61B 5/0464* (2013.01); *A61B 5/4848* (2013.01); *A61N 1/3962* (2013.01); *A61N 1/368* (2013.01); *A61N 1/3622* (2013.01)

(58) Field of Classification Search
CPC .................................................... A61N 1/3754
USPC ............................... 600/510, 518; 607/14, 27
See application file for complete search history.

(56) References Cited

U.S. PATENT DOCUMENTS 5,193,550 A * 3/1993 Duffin ........................... 600/510
5,228,438 A * 7/1993 Buchanan ....................... 607/18
(Continued)

FOREIGN PATENT DOCUMENTS

WO         01/24874 A1     4/2001

OTHER PUBLICATIONS

Wang, PJ et al., Clinical Cardiac Pacing, Defibrillation, and Resynchronization Therapy (Third Edition) Section 4: Follow-Up and Programming, Chapter 28: Timing Cycles of Implantable Devices (Jan. 2007) pp. 813-843.
(Continued)

*Primary Examiner* — Christopher A Flory
(74) *Attorney, Agent, or Firm* — Scully, Scott, Murphy & Presser, P.C.

(57) ABSTRACT

Dual chamber pacemaker systems can lead to two forms of pacemaker-facilitated tachycardia—pacemaker-mediated tachycardia (PMT) and tracking of sinus or atrial tachycardia. Current pacemaker algorithms can not always differentiate between these two tachycardias. Various embodiments for differentiating these particular mechanisms of pacemaker-facilitated tachycardia, which is based on the specific termination response to PVARP extension are provided. The response to PVARP extension (V-A-A-V vs V-A-V) is a specific method for differentiation and can be used in conjunction with observations of atrial rate and electrogram morphology (or surface P wave morphology) for distinguishing between the two mechanisms of pacemaker-facilitated tachycardia.

19 Claims, 8 Drawing Sheets

(51) Int. Cl.
*A61N 1/39* (2006.01)
*A61B 5/0464* (2006.01)
*A61B 5/00* (2006.01)
*A61N 1/362* (2006.01)
*A61N 1/368* (2006.01)

(56) References Cited

U.S. PATENT DOCUMENTS

| | | | | |
|---|---|---|---|---|
| 5,247,929 | A | * | 9/1993 | Stoop et al. ............ 607/14 |
| 5,312,450 | A | * | 5/1994 | Markowitz ............ 607/14 |
| 5,423,868 | A | * | 6/1995 | Nappholz et al. ............ 607/14 |
| 5,496,350 | A | | 3/1996 | Lu |
| 5,507,783 | A | * | 4/1996 | Buchanan ............ 607/14 |
| 5,514,164 | A | | 5/1996 | Mann et al. |
| 5,674,255 | A | * | 10/1997 | Walmsley et al. ............ 607/14 |
| 6,285,908 | B1 | * | 9/2001 | Mann et al. ............ 607/28 |
| 6,564,095 | B1 | * | 5/2003 | Stahl et al. ............ 607/14 |
| 7,551,961 | B1 | * | 6/2009 | Pei et al. ............ 607/9 |
| 2004/0210266 | A1 | * | 10/2004 | Kramer ............ 607/25 |
| 2006/0089676 | A1 | * | 4/2006 | Rottenberg et al. ............ 607/14 |
| 2007/0244521 | A1 | * | 10/2007 | Bornzin et al. ............ 607/9 |
| 2008/0269826 | A1 | | 10/2008 | Lian et al. |
| 2010/0286743 | A1 | * | 11/2010 | Enrooth et al. ............ 607/28 |

OTHER PUBLICATIONS

Nitzsché, R, "Endless-loop tachycardias: description and first clinical results of a new fully automatic protection algorithm" Pacing Clin Electrophysiol (Dec. 1990) pp. 1711-1718, vol. 13.

McAlister HF, et al., "Atrial electrogram analysis: antegrade versus retrograde" Pacing Clin Electrophysiol (Nov. 1988) pp. 1703-1707, vol. 11.

Tzeis, S. et al., "Two Types of Narrow-QRS Tachycardia in a Patient with Coarctation of the Aorta and Persistent Left Superior Vena Cave" Hellenic Journal of Cardiology (Dec. 31, 2009) pp. 548-551, vol. 50, No. 6.

International Search Report dated Aug. 22, 2012, issued in International Application No. PCT/US2011/064970.

* cited by examiner

METHOD, DEVICE AND PROGRAM TO DIFFERENTIATE PACEMAKER-MEDIATED TACHYCARDIA (PMT) FROM TRACKING OF SINUS OR ATRIAL TACHYCARDIA (AT)

CROSS-REFERENCE TO RELATED APPLICATIONS

This application claims the benefit of and priority to U.S. provisional application Ser. No. 61/422,779 filed on Dec. 14, 2010.

BACKGROUND

The most common cause of pacemaker-facilitated tachycardia is pacemaker-mediated tachycardia (PMT), also commonly known as endless loop tachycardia. Continuous retrograde conduction through the AV node during ventricular paced beats results in an ongoing loop of atrial sensed—ventricular paced beats. Pacemaker algorithms for identifying and treating PMT are well recognized and effective. Less common and often unrecognized or misdiagnosed is pacemaker-facilitated tachycardia due to atrial tracking. (Wang P J, Chen H, Okamura H, Al-Ahmad A, Hsia H H: Timing Cycles of Implantable Devices. In Ellenbogen K A, Kay G N, Lau C P, Wilkoff B L, eds: Clinical Cardiac Pacing, Defibrillation, and Resynchronization Therapy. $3^{rd}$ Edition. Philadelphia: WB Saunders, 2007, pp. 969-1004, hereinafter "Wang") In this circumstance, sinus or atrial tachycardia triggers ventricularly paced beats when the programmed sensed AV interval (SAV) is less than the intrinsic AV interval. In the absence of identifiable P waves, ECG discrimination between these arrhythmias is often indistinct. Furthermore, current pacemaker algorithms are unable to differentiate between these two tachycardias.

We introduce a new method for identifying each of these particular mechanisms of pacemaker-facilitated tachycardia, which is based on the specific termination response to post-ventricular atrial refractory period extension (PVARP).

SUMMARY

A system, a device, a method and a program to distinguish between the two forms of pacemaker-facilitated tachycardia based on the response to PVARP extension. In the presence of intact AV conduction, the V-A-V response is specific to atrial (or sinus) tachycardia, while the V-A-A-Vs response is specific to PMT. When a V-A-A-Vp response is observed, the atrial rate during tachycardia and following the PVARP extension maneuver is used to classify the mechanism. Finally, in the rare case of an isorhythmic atrial rate with a V-A-A-Vp response, the atrial electrogram morphology (or surface P wave morphology) can distinguish PMT from atrial tracking. The method was validated using a virtual simulator. The method also may include a remote alert system. The invention also includes treating the patient according to methods known in the art.

Disclosed is a method to distinguish pacemaker-mediated tachycardia (PMT) from tracking of sinus or atrial tachycardia (AT) comprising:

analyzing, using a processor, a response to an extension of a post-ventricular atrial refractory period, by classifying the response into responsive patterns; and determining, using the processor, a mechanism of a tachycardia based at least upon the classifying wherein a V-A-V response is specific to atrial or sinus tachycardia, and a V-A-A-Vs response is specific to PMT, and wherein if a V-A-A-Vp response is observed, the method further comprises:

comparing, using the processor, an atrial rate during the tachycardia and an atrial rate after the PVARP extension; and determining, using the processor, a mechanism of the tachycardia based at least upon the comparison, wherein a slower atrial rate after the PVARP extension is specific to PMT.

Also disclosed is a computer readable storage medium having a program for causing a processor to execute a method to distinguish pacemaker-mediated tachycardia (PMT) from tracking of sinus or atrial tachycardia (AT) comprising:

analyzing a response to an extension of a post-ventricular atrial refractory period by classifying a response by responsive patterns; and determining a mechanism of the tachycardia based at least upon the classifying wherein a V-A-V response is specific to atrial or sinus tachycardia, a V-A-A-Vs response is specific to PMT, and wherein if a V-A-A-Vp response is observed, and the method further comprises:

comparing an atrial rate during the tachycardia and an atrial rate after the PVARP extension; and determining a mechanism of the tachycardia based at least upon the comparison, wherein a slower atrial rate after the PVARP extension is specific to PMT.

Also disclosed is a chronic implantable electronic device (CIED) comprising:

a storage device configured to store a computer readable program, a processor, configured to, when executing the computer readable program provide:

an analyzing unit configured to analyze a response to an extension of a post-ventricular atrial refractory period, by classifying the response into responsive patterns;

a determining unit configured to determine a mechanism of a tachycardia based at least upon the classifying; and a comparing unit configured to compare an atrial rate during the tachycardia and an atrial rate after the PVARP extension wherein a V-A-V response is specific to atrial or sinus tachycardia, and a V-A-A-Vs response is specific to PMT, and wherein if a V-A-A-Vp response is observed, the determining unit is configured to also use a result of the comparing to determine a mechanism of the tachycardia, a slower atrial rate after the PVARP extension is specific to PMT.

DETAILED DESCRIPTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims. The contents of all cited references (including literature references, issued patents, and published patent applications as cited throughout this application) are hereby expressly incorporated by reference.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

We created and tested the utility of a method to distinguish between the two forms of pacemaker-facilitated tachycardia based on the response to PVARP extension. In the presence of intact AV conduction, the V-A-V response is specific to atrial (or sinus) tachycardia, while the V-A-A-Vs response is specific to PMT. When a V-A-A-Vp response is observed, the atrial rate during tachycardia and following the PVARP extension maneuver is used to classify the mechanism. Finally, in the rare case of an isorhythmic atrial rate with a V-A-A-Vp response, the atrial electrogram morphology (or surface P wave morphology) can distinguish PMT from atrial tracking. The method was validated using a virtual simulator.

Distinguishing between pacemaker-facilitated tachycardia due to PMT and atrial tracking has proved to be an elusive diagnostic dilemma as pacemakers often miscategorize the mechanism. These two forms of tachycardia can be terminated by magnet application or PVARP extension. Magnet application changes the tracking mode (DDD) to an asynchronous mode (DOO). With PVARP extension, retrograde or antegrade atrial sensed events can no longer trigger a SAV delay and be tracked. Although these maneuvers are effective means of termination for both forms of tachycardia, they do not permit mechanistic differentiation. Recognizing the difference between the tachycardias has important implications for pacemaker programming. If the atrial tracking were misdiagnosed as PMT, programming a longer PVARP, particularly in a patient with preexisting prolonged VA conduction, would decrease the maximum tracking rate and diminish exercise capacity.

Figures 3A, 3B, 3C, 3D:
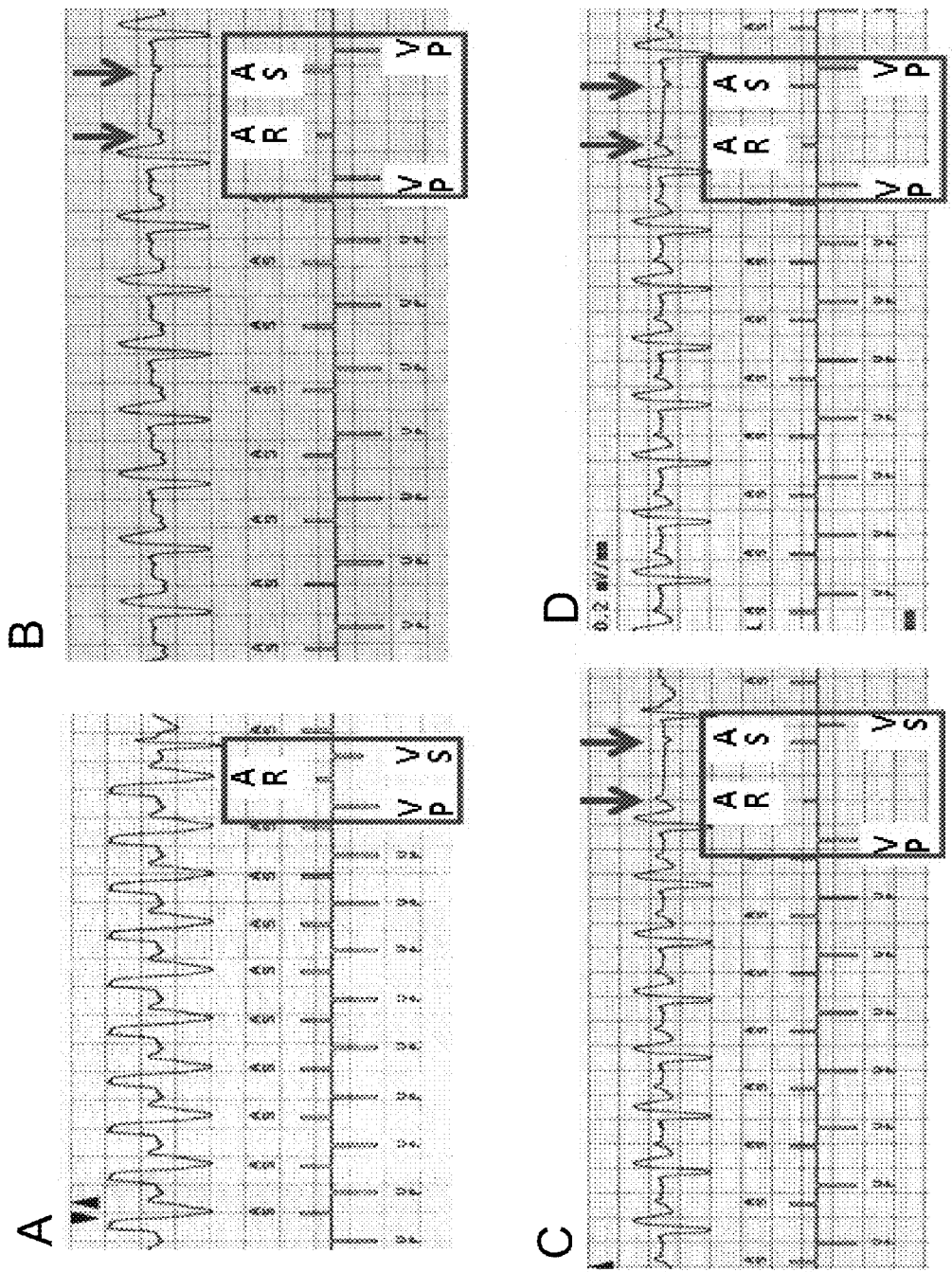
FIG. 3. Examples of surface electrocardiograms (top) and marker channels (bottom) recorded during simulator experiments during the four tested scenarios. A. Response to PVARP extension during an atrial tachycardia with intact AV conduction. Note the V-A-Vs response (red circle). B. Response to PVARP extension during an atrial tachycardia with underlying complete heart block. Note the V-A-A-Vp response (red circle) and the unchanged P wave morphology. C. Response to PVARP extension during PMT with intact underlying AV conduction. Note the V-A-A-Vs response (red circle). Although the background atrial rate is similar to the PMT rate, the surface electrocardiogram shows a positive P wave during retrograde atrial conduction and a negative P wave during antegrade atrial conduction. D. Response to PVARP extension during PMT with underlying CHB. Note the V-A-A-Vp response (red circle). Although the background atrial rate is similar to the PMT rate, the changing P wave morphology on the surface electrocardiogram helps categorize this scenario as PMT rather than tracking of atrial (or sinus tachycardia).

A prolonged VA interval (longer than the programmed PVARP) and delayed intrinsic AV nodal conduction and/or a short programmed sensed AV delay facilitates the development of atrial tracking from either sinus/atrial tachycardia or PMT. Our study illustrates that methods for distinguishing between the two forms of tachycardia include comparing the atrial rate and atrial electrogram morphology during tachycardia and following the PVARP extension maneuver. However, the finding most informative and specific for identifying the correct mechanism of the tachycardia is the pattern of termination following PVARP extension (V-A-V vs V-A-A-V response). PMT occurs when a ventricular event (either spontaneous or paced) is able to conduct retrogradely through the AV node. The As event then begins a SAV delay, which results in a Vp event. In PMT, this sequence is iterative. (Wang) In the scenario of a single PVARP extension, the tachycardia terminates because the immediate retrograde atrial event is not sensed (Ar) and therefore does not trigger a SAV delay, or a Vp event, nor does an intrinsic ventricular beat occur due to antegrade AV nodal refractoriness. (Nitzsché R, Gueunoun M, Lamaison D, Lascault G, Pioger G, Richard M, Malherbe O, Limousin M. Endless-loop tachycardias: description and first clinical results of a new fully automatic protection algorithm. Pacing Clin Electrophysiol. 1990; 13:1711-8.) The next ventricular beat (Vp or Vs) can only occur in response to the next As event: either Vp if intrinsic AV conduction is absent or longer than the programmed SAV delay or Vs if it is less than the programmed SAV delay with corresponding termination of tachycardia (FIGS. 3C & 3D). Termination of PMT is therefore obligatorily associated with a V-A-A-V response unless dual AV nodal pathways are present and antegrade conduction of one of the pathways remains intact; this would be associated with a Vp-Ar-Vs response.

Figure 1:
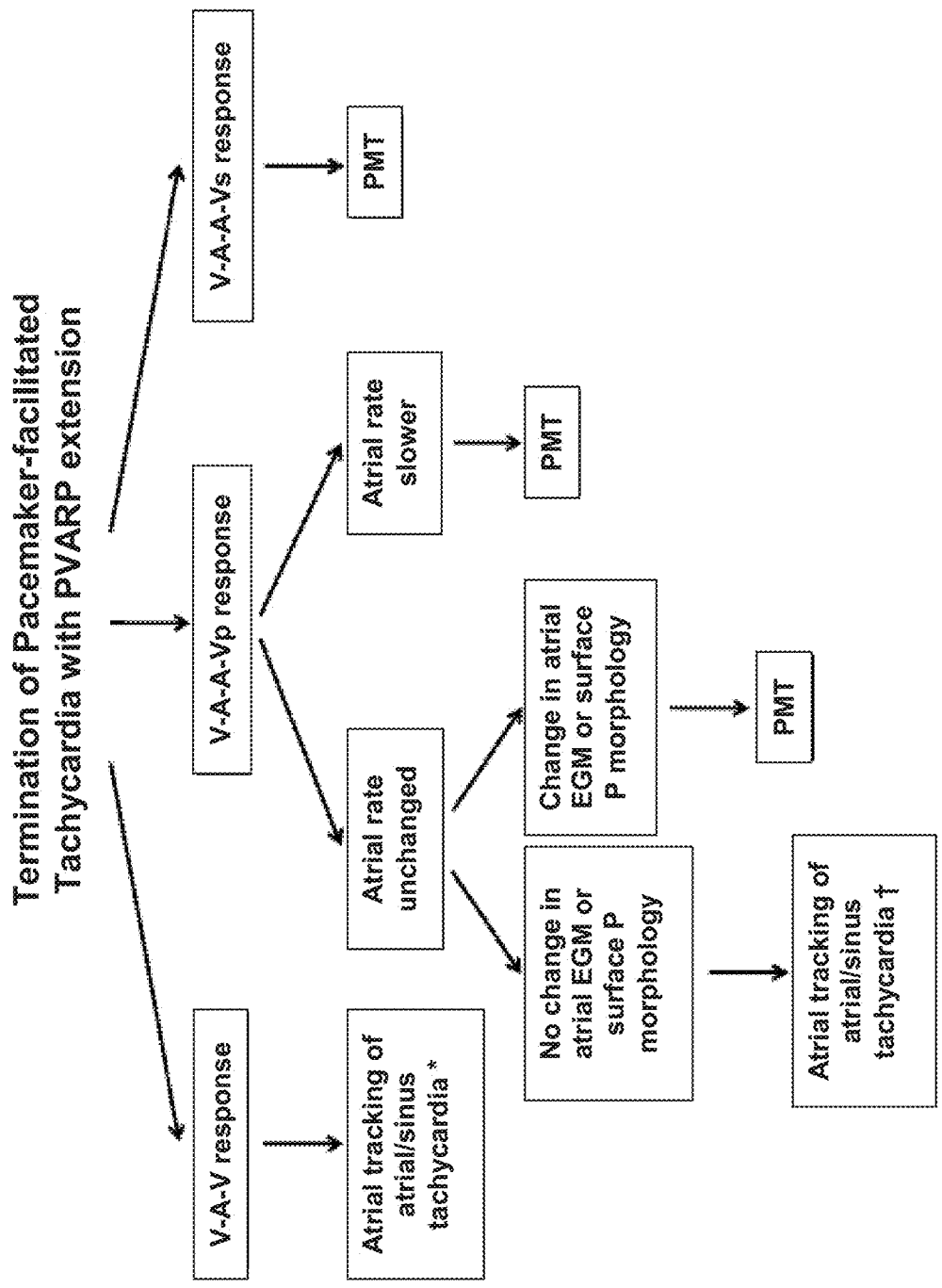
FIG. 1. Method for differentiating between the two types of pacemaker-facilitated tachycardia—atrial tracking due to atrial (or sinus) tachycardia vs pacemaker-mediated tachycardia (PMT). *Except in the case of PMT and dual AVN pathways. †V-A-A-V response only occurs when there is an absence of intrinsic AV conduction. See text for discussion. EGM=electrogram; PMT=pacemaker-mediated tachycardia; Vp=ventricular paced event; Vs=ventricular sensed event.
Figure 2:
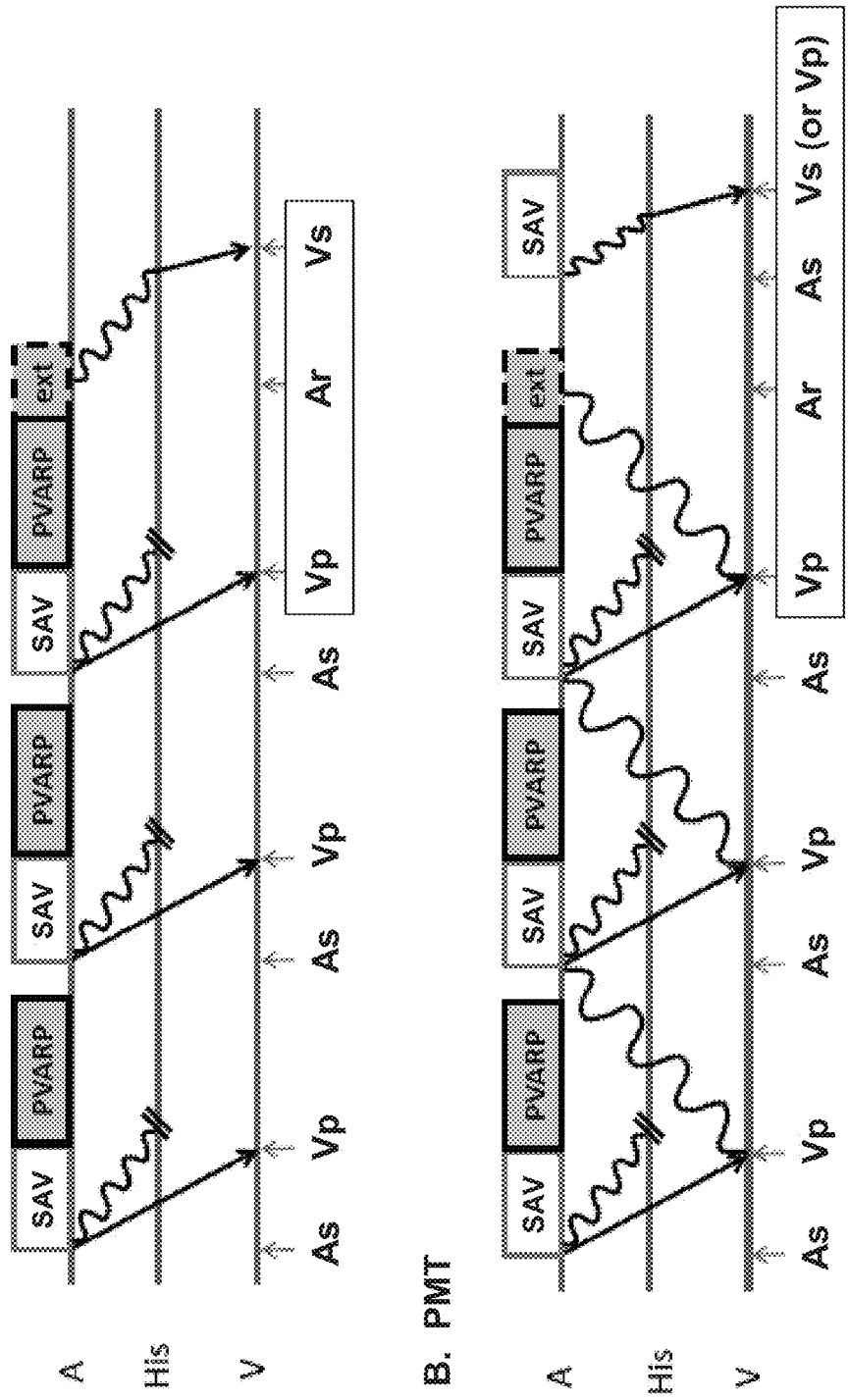
FIG. 2. Response after single post ventricular atrial refractory period (PVARP) extension. A. During atrial tracking in DDD mode of atrial (or sinus) tachycardia, PVARP extension transforms the atrial event into an AR event and tracking no longer continues. This results in a V-A-V response and termination of wide complex tachycardia in the case of intact AV conduction. B. During PMT, PVARP extension beyond the retrograde atrial event can no longer trigger a SAV delay and the tachycardia terminates, resulting in a V-A-A-V response. See text for discussion. As=atrial sensed event; Ar=atrial refractory event; ext=extension; PVARP=post ventricular atrial refractory period, SAV=sensed atrioventricular delay.

When atrial (or sinus) tachycardia is tracked in DDD mode and the PVARP is sufficiently extended, the atrial event is transformed into an Ar event and tracking can no longer perpetuate (FIG. 2A). The result is either a V-A-V and termination of tachycardia in the case of intact AV conduction (FIG. 3A) or V-A-A-Vp response and perpetuation of tachycardia if AV conduction is absent or prolonged (FIG. 3B). When a V-A-A-Vp response occurs and the tachycardia rate remains unchanged, the diagnosis is more likely to be atrial tracking rather than PMT (which is usually associated with a sudden change in the tachycardia cycle length, unless there is underlying isorhythmic sinus/atrial tachycardia). However, in the setting of exercise, as observed in our patient or atrial tachycardia, this distinguishing feature is no longer reliable. Therefore, the V-A-V response is helpful in the specific case of intact AV conduction, which may become more apparent due to loss of concealed retrograde invasion of the AV node during ventricular pacing. When a V-A-A-Vp response occurs and the atrial tachycardia rate remains unchanged, the diagnosis is more likely to be atrial tracking rather than PMT and the atrial electrogram or surface P wave morphology can be used to confirm the diagnosis.

Therefore, in addition to a V-A-V termination response, evidence to suggest that pacemaker-facilitated WCT is due to atrial tracking includes the following observations: (1) the atrial rate remains unchanged following termination of WCT (FIG. 3A, B), and (2) the morphology of the atrial EGM remains unchanged in WCT compared with sinus rhythm (FIG. 4B, C). Since the vector of atrial activation during PMT is inferior to superior, one would expect a change in local atrial electrogram morphology upon termination. The use of such near-field signals from bipolar leads for the purpose of morphology discrimination between antegrade and retrograde atrial activation is limited. (McAlister H F, Klementowicz P T, Calderon E M, Benedek Z M, Furman S. Atrial electrogram analysis: antegrade versus retrograde. Pacing Clin Electrophysiol. 1988; 11:1703-7) However, if used in combination with the above observations, most cases of pacemaker-facilitated tachycardia can be properly categorized. Additional information regarding the shift of the P wave axis can be further elucidated if the surface electrogram or its equivalent (i.e. far field electrogram) is available for review.

The method may also include a step of providing an alert of the diagnosis or need for further steps, for example but without limitation, to the treating physician via a device remote alert systems as are known in the art. Therefore, device remote alert systems will not be described in detail.

If the method produces a diagnosis of PMT, the physician should provide the standard of care in the art. Alternatively, a device, such as a chronic implantable electronic device can automatically respond to the diagnosis. As of the date of this filing this could include performing any or all of the following:

a. program "ON" PMT interventions (i.e. single PVARP extension to 480-500 msec)

b. program "ON" PVC response (a PMT prevention algorithm that extends PVARP following a device-classified PVC (a ventricular sensed event without a preceding atrial sensed or atrial paced event).

c. increase baseline PVARP to greater than retrograde atrial activation from ventricular pacing (this may vary depending on the clinical scenario and the pre-existing timing cycles, such as sensed AV delay and upper tracking rate, in order to minimize pacemaker upper rate behavior)

If the method produces a diagnosis of AT, the physician should provide the standard of care in the art. As of the date of this filing this could include performing any or all of the following:

a. medications (titration or initiation of AV nodal blockers and/or anti-arrhythmic drugs)

b. ablation procedure c. intervention with anti-tachycardia pacing/cardioversion.

As will be appreciated by one skilled in the art, the present invention may be embodied as a system, such as, but not limited to, an external device and a chronic implantable electronic device (CIED) such as cardiac pacemaker or implantable cardioverter-defibrillator (ICD); a device, such as, but not limited to, a cardiac pacemaker or ICD; a method or computer program product. A CIED can include, but is not limited to, at least one storage device and processor. The storage device(s) stores a computer readable program and a correspondence between responsive patterns and mechanisms of a tachycardia. The processor analyzes a response to an extension of a post-ventricular atrial refractory period, by classifying the response into responsive patterns, and determines a mechanism of a tachycardia based at least upon the classification with reference to the correspondence in the storage device and compares an atrial rate during the tachycardia and an atrial rate after the PVARP extension, if needed. Thus, the processor acts as an analyzing unit, a determining unit and a comparing unit.

Additionally, aspects of the invention can be implemented by an external processor configured to receive and process signals from an electrogram system. Thus, the external processor acts as an analyzing unit, a determining unit and a comparing unit.

Various aspects of the present invention may be embodied as a program, software, or computer instructions embodied or stored in a computer, processor or machine usable or readable medium, which causes the computer, processor, or machine to perform the method when executed on the computer, processor, and/or machine.

A computer readable medium, tangibly embodying a program of instructions executable by a machine to perform various functionalities and methods described in the present invention is also provided.

The computer readable medium could be a computer readable storage medium or a computer readable signal medium. Regarding a computer readable storage medium, it may be, for example, a magnetic, optical, electronic, electromagnetic, infrared, or semiconductor system, apparatus, or device, or any suitable combination of the foregoing; however, the computer readable storage medium is not limited to these examples. Additional particular examples of the computer readable storage medium can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an electrical connection having one or more wires, an optical fiber, an optical storage device, or any appropriate combination of the foregoing; however, the computer readable storage medium is also not limited to these examples. Any tangible medium that can contain, or store a program could be a computer readable storage medium.

EXAMPLES

The present description is further illustrated by the following examples, which should not be construed as limiting in any way.

Example 1

Simulation

We prospectively tested this method using the Medtronic Virtual Interactive patient (VIP) II, Version 1.53 (Minneapolis, Minn.) and a Medtronic Adapta ADDR01 dual chamber pacemaker. The simulator allows programming of intrinsic antegrade and retrograde VA conduction as well as atrial rates and is capable of introducing PVCs. Thirty-five scenarios (listed in Table 1) were derived from calculating the rates necessary to trigger PMT detection by the Medtronic device. The pacemaker assumes that PMT may be present when it detects a ninth ventricular paced event (Vp) following eight consecutive VA intervals that meet all of the following conditions: (1) duration less than 400 ms, (2) starts with a Vp event, and (3) ends with an atrial sensed (As) event.

TABLE 1

Programming parameters used for evaluating the response to PVARP extension during atrial tachycardia and PMT.

| | | Simulator (Patient) Parameters (in msec) | | | Pacemaker Parameters (in msec) | | | |
|---|---|---|---|---|---|---|---|---|
| | CHB | Intrinsic VA | Intrinsic atrial rate | Intrinsic AV | Lower rate | Upper rate | SAV | PVARP | Response |
| AT with intact AV conduction |
| 1 | No | 0 | 130 | 125 | 60 | 135 | 120 | 340 | V-A-V |
| 2 | No | 0 | 145 | 125 | 60 | 150 | 120 | 290 | V-A-V |
| 3 | No | 0 | 165 | 125 | 60 | 170 | 120 | 240 | V-A-V |
| 4 | No | 0 | 190 | 135 | 60 | 195 | 120 | 190 | V-A-V |
| 5 | No | 0 | 125 | 155 | 60 | 130 | 150 | 320 | V-A-V |
| 6 | No | 0 | 135 | 155 | 60 | 140 | 150 | 260 | V-A-V |
| 7 | No | 0 | 155 | 155 | 60 | 160 | 150 | 220 | V-A-V |
| 8 | No | 0 | 175 | 155 | 60 | 180 | 150 | 190 | V-A-V |
| 9 | No | 0 | 115 | 190 | 60 | 120 | 180 | 330 | V-A-V |
| 10 | No | 0 | 130 | 190 | 60 | 135 | 180 | 260 | V-A-V |
| 11 | No | 0 | 140 | 190 | 60 | 145 | 180 | 230 | V-A-V |
| 12 | No | 0 | 160 | 190 | 60 | 165 | 180 | 190 | V-A-V |
| AT with complete heart block |
| 13 | Yes | 0 | 145 | NA | 60 | 150 | 120 | 290 | V-A-A-Vp |
| 14 | Yes | 0 | 165 | NA | 60 | 170 | 120 | 240 | V-A-A-Vp |
| 15 | Yes | 0 | 190 | NA | 60 | 195 | 120 | 190 | V-A-A-Vp |
| 16 | Yes | 0 | 125 | NA | 60 | 130 | 150 | 320 | V-A-A-Vp |
| 17 | Yes | 0 | 135 | NA | 60 | 140 | 150 | 260 | V-A-A-Vp |
| 18 | Yes | 0 | 155 | NA | 60 | 160 | 150 | 220 | V-A-A-Vp |
| 19 | Yes | 0 | 175 | NA | 60 | 180 | 150 | 190 | V-A-A-Vp |
| 20 | Yes | 0 | 115 | NA | 60 | 120 | 180 | 330 | V-A-A-Vp |
| 21 | Yes | 0 | 130 | NA | 60 | 135 | 180 | 260 | V-A-A-Vp |
| 22 | Yes | 0 | 140 | NA | 60 | 145 | 180 | 230 | V-A-A-Vp |
| 23 | Yes | 0 | 160 | NA | 60 | 165 | 180 | 190 | V-A-A-Vp |
| PMT with intact AV conduction |
| 24 | No | 350 | 115 | 140 | 60 | 130 | 150 | 320 | V-A-A-Vs |
| 25 | No | 300 | 125 | 140 | 60 | 140 | 150 | 260 | V-A-A-Vs |
| 26 | No | 250 | 140 | 140 | 60 | 160 | 150 | 220 | V-A-A-Vs |
| 27 | No | 200 | 160 | 140 | 60 | 180 | 150 | 190 | V-A-A-Vs |
| PMT with complete heart block |
| 28 | Yes | 350 | 115 | NA | 60 | 130 | 150 | 320 | V-A-A-Vp |
| 29 | Yes | 300 | 125 | NA | 60 | 140 | 150 | 260 | V-A-A-Vp |
| 30 | Yes | 250 | 140 | NA | 60 | 160 | 150 | 220 | V-A-A-Vp |
| 31 | Yes | 200 | 160 | NA | 60 | 180 | 150 | 190 | V-A-A-Vp |
| 32 | Yes | 350 | 105 | NA | 60 | 120 | 180 | 330 | V-A-A-Vp |
| 33 | Yes | 300 | 115 | NA | 60 | 135 | 180 | 260 | V-A-A-Vp |
| 34 | Yes | 250 | 130 | NA | 60 | 145 | 180 | 230 | V-A-A-Vp |
| 35 | Yes | 200 | 145 | NA | 60 | 165 | 180 | 190 | V-A-A-Vp |

AT = atrial tachycardia;
CHB = complete heart block.

In order to initiate PMT, several pre-specified retrograde VA intervals were chosen (350 ms, 300 ms, 250 ms, and 200 ms). The pacemaker was set to PVARP 20-40 ms shorter than the retrograde VA interval, SAV delays of 150 or 180 ms and a baseline atrial rates of 80 bpm. PMT was initiated by introducing a PVC during sinus rhythm. To simulate an isorhythmic atrial rhythm, the atrial rate was then programmed 2-6 bpm slower than the PMT rate in each scenario. The PMT intervention was then programmed ON, which, following detection of eight consecutive Vp-As intervals, extends PVARP to 400 ms after the ninth paced ventricular event. The response to PVARP extension was recorded in the presence of either normal AV nodal conduction or complete AV block.

In order to simulate sinus or atrial tachycardia, the VIP II simulator was programmed to have an intrinsic atrial rate ranging 130-175 bpm (less than the nominal mode switch rate of 180 bpm), with a PR interval 5-10 ms longer than the corresponding pacemaker SAV delay setting (120, 150, 180 ms). The retrograde VA conduction was programmed OFF (to prohibit the possibility of PMT), and the PVARP was set 5-35 ms shorter than the value of total atrial refractory period (TARP) that would cause 2:1 block. During the tachycardia, the response to PVARP extension was recorded in the presence of either normal AV conduction or complete AV block.

Results

A total of 35 scenarios were tested, and the sequence of atrial sensed (As), atrial refractory (Ar), ventricular paced (Vp), and ventricular sensed (Vs) events were noted following a single PVARP extension during tachycardia (see Table 1). All 12 scenarios of atrial tachycardia with intact AV conduction terminated with a Vp-Ar-Vs (V-A-V) response as a result of PVARP extension (FIG. 3A). Of the 11 scenarios of atrial tachycardia with complete heart block (Table 1), all 11 terminated with a Vp-Ar-As-Vp (V-A-A-Vp) response (FIG. 3B). All of the 4 episodes of PMT with intact AV conduction terminated with a Vp-Ar-As-Vs (V-A-A-Vs) response (FIG. 3C). Finally, of the 8 episodes of PMT with absent antegrade AV conduction, all 8 terminated with a Vp-Ar-As-Vp (V-A-A-Vp) response (FIG. 3D).

FIG. 3A demonstrates the V-A-V response that is specific to atrial tracking of sinus or atrial tachycardia. When a pacemaker-defined PMT is detected, PVARP is extended to 400 ms and transforms the atrial event into an atrial refractory (Ar) event. Therefore, tracking (and the subsequent Vp event) does not occur for the corresponding beat; however, an intrinsic Vs event occurs because AV nodal conduction is intact. A schematic of this mechanism is shown in FIG. 2A.

Although the simulated local atrial electrogram is not informative in identifying the origin of atrial activation, the simulator generates a surface electrogram that allows assessment of P wave axis. The surface electrocardiogram shows a positive P wave during retrograde atrial conduction and a negative P wave during antegrade atrial conduction. In the situation of intact AV conduction, PMT terminated following PVARP extension with a Vp-Ar-As-Vs (V-A-A-Vs) response (FIG. 3C). The morphology of the surface P wave remains the same on the Ar beat due to continued retrograde AV conduction during PMT. However, the subsequent beat no longer originates from retrograde conduction and the P wave axis shifts accordingly on the surface electrocardiogram. A V-A-A-Vs response following PVARP extension is specific to PMT with intact AV conduction because an atrial (or sinus) tachycardia would conduct antegrade following the first atrial (Ar) event if intact AV nodal conduction were preserved. A schematic of this response is shown in FIG. 2B.

A V-A-A-Vp response to PVARP extension was observed with both atrial (or sinus) tracking with AV block and PMT. In the situation of tracking of an atrial (or sinus) tachycardia with complete heart block (FIG. 3B), a V-A-A-Vp response occurs, the atrial rate following PVARP extension remains the same as the rate during tachycardia, and the atrial electrogram morphology (or surface P wave morphology) is identical.

Following a V-A-A-Vp response, if the post PVARP extension rate is significantly less than the tachycardia rate, the diagnosis is PMT. However, since the scenarios tested a background atrial rate that was only slightly slower than the PMT rate (simulating the rare case of an isorhythmic atrial rhythm without a V-A-V response), this distinguishing feature could not be used. As seen in FIG. 3D, the scenario of PMT with complete heart block resulted in a V-A-A-Vp response with a similar post-termination atrial rate. Upon closer inspection, the morphology of the surface P wave remained the same as during PMT on the Ar beat but the subsequent As beat resulted in a P wave axis shift on the surface electrogram, thus confirming the diagnosis of PMT.

Example 2

Illustrative Case

A 57-year-old man had a dual chamber pacemaker implanted for exercise-induced atrioventricular block (St. Jude Medical Model Victory XL DR 5816, SJM model 199TC active bipolar lead placed in the right atrial appendage, and SJM model 1888TC active bipolar lead placed in the right ventricular apex). The programmed mode was DDD with a lower rate of 45 bpm and a maximum tracking rate (MTR) of 160 bpm. The paced/sensed AV delays (PAV/SAV) were 180/180 ms. The rate responsive AV delay was programmed to "low" with the shortest AV delay 100 ms. The PVARP was 200 ms and rate responsive PVARP was programmed to "low" with the shortest PVARP 170 ms. The atrial tachycardia detection rate (mode switch rate) was 180 bpm.

Figure 4A:
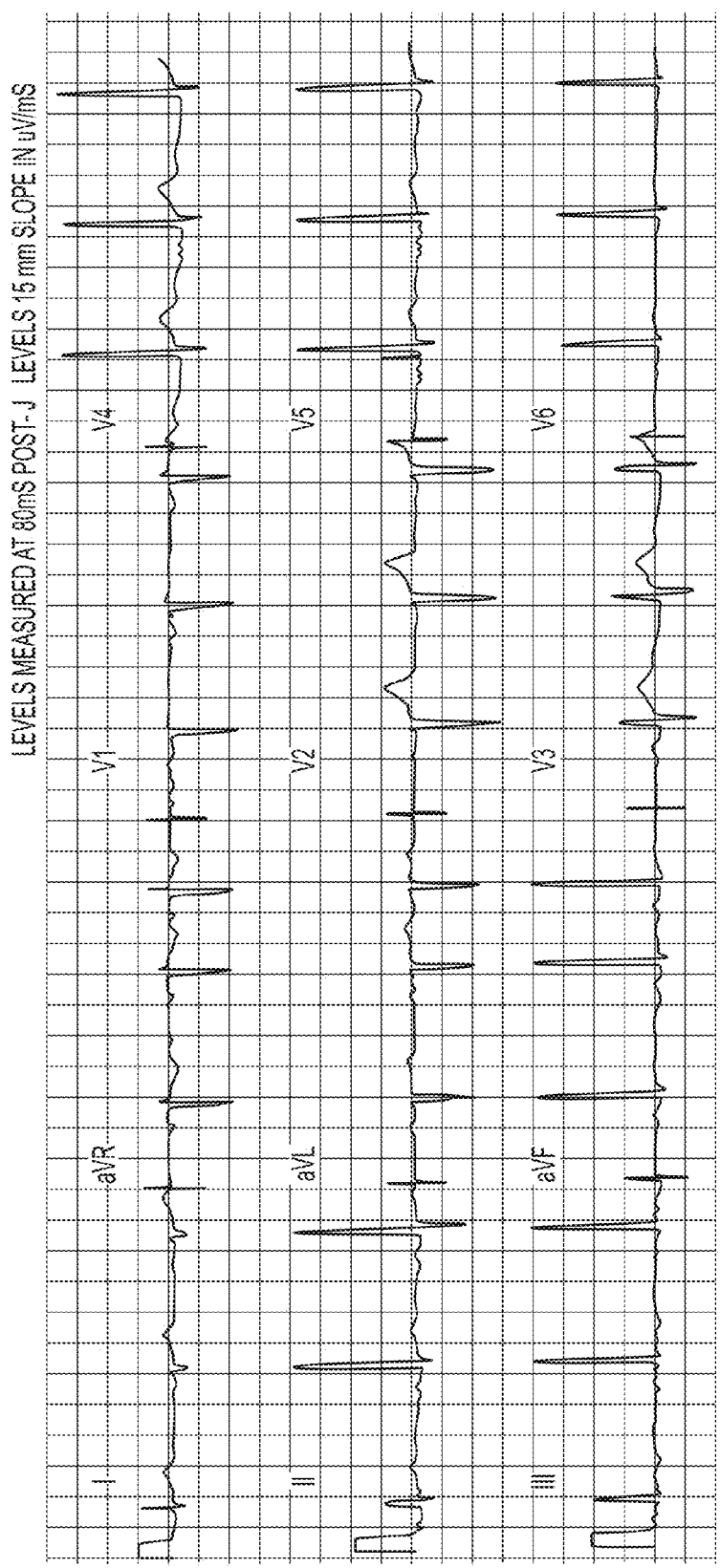
FIG. 4. ECGs from introductory case. A: Sinus rhythm ECG. B: Wide complex tachycardia during exercise. Frequent spontaneous ventricular ectopy superimposed during ventricular pacing created the appearance of polymorphic ventricular tachycardia.
Figure 4B:
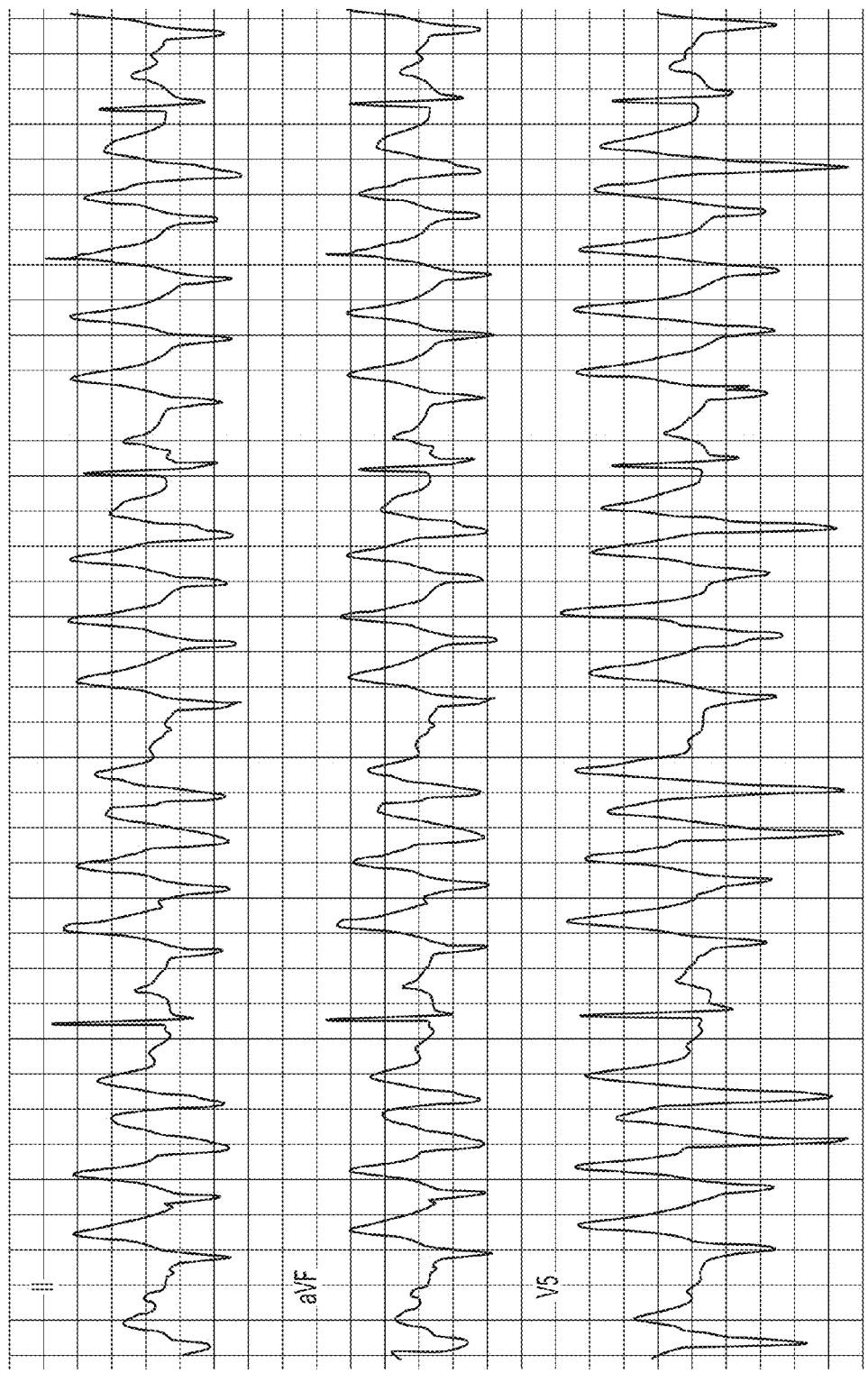
Figure 5A:
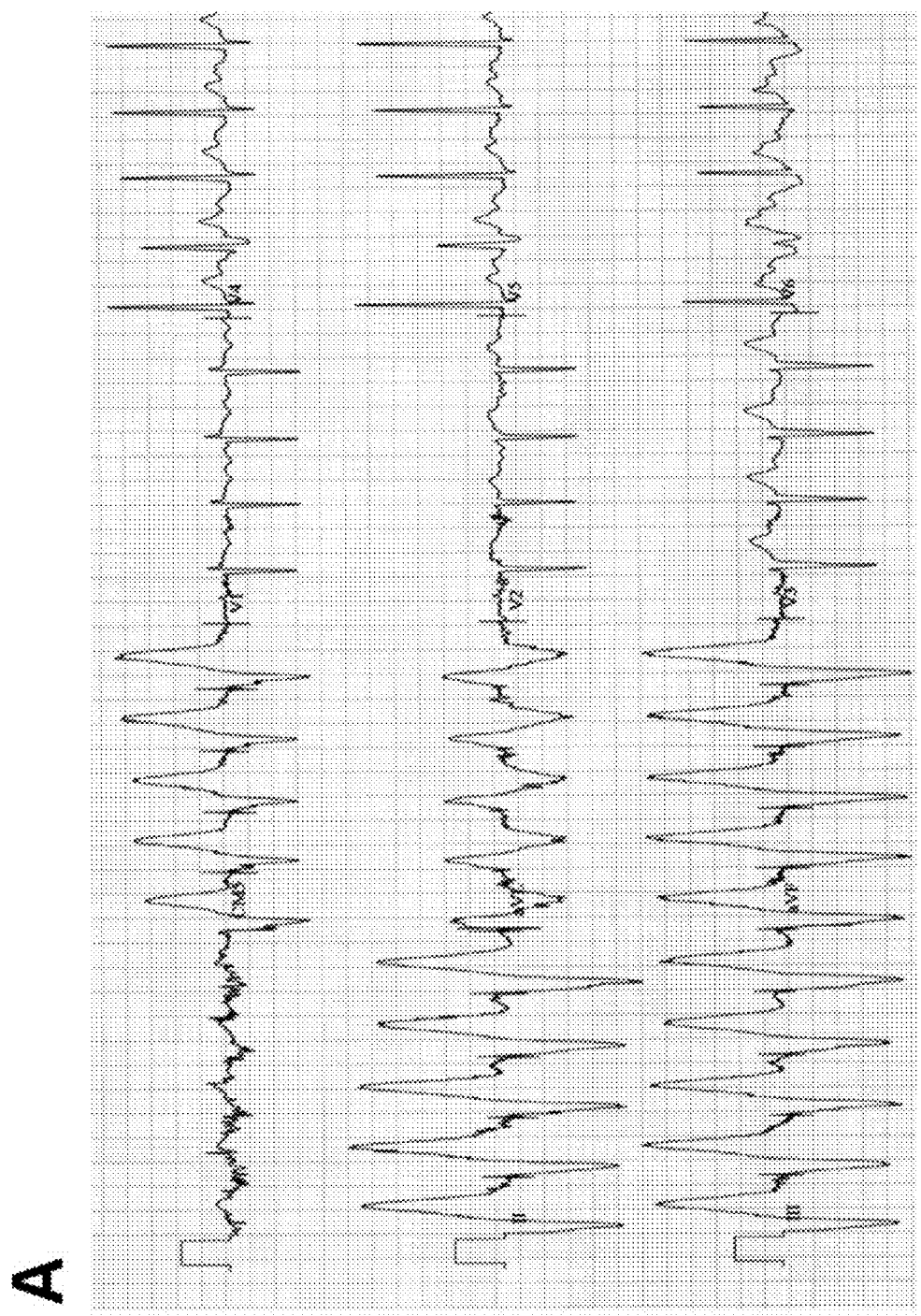
FIG. 5. Termination of wide complex tachycardia (WCT) with extension of PVARP. A. 12-lead ECG showing termination of WCT after extending PVARP from 200 ms to 375 ms. B. Device electrograms obtained simultaneously when FIG. 4A was obtained. Note the change in the morphology of the local ventricular electrogram (arrows) with termination of WCT; however, the local atrial electrogram morphology remains unchanged (asterisks), suggesting that the pacemaker-facilitated tachycardia was due to tracking of sinus tachycardia. Termination of WCT is also associated with a V-A-V response (black circle). C. "PMT detection" terminates WCT with a single PVARP extension. The pacemaker detection algorithm miscategorizes the episode as PMT (black box) since ten consecutive atrial sensed—ventricular paced (AS-VP) beats exceeded a set PMT detection rate. In response to such an event, the device resets the PVARP to 480 ms for a single cycle after the $10^{th}$ AS-VP event, rendering the device unresponsive to retrograde P waves, terminating the WCT with a V-A-V response (black circle). This finding was consistent with atrial tracking during sinus tachycardia rather than PMT caused by retrograde atrial activation. (In the patient's device, rate responsive AV delay shortens the AV delay settings by 1 ms for every 1 bpm change in the pacing rate with the "low" setting until the minimum AV delay is reached. The algorithm starts to operate when rate rises above 90 bpm). When the patient was exercising to a heart rate of 160 bpm, his SAV shortened to 100 ms and he started pacing in response to his sinus tachycardia. See text for discussion. AS without black box=atrial sensed event; AS within black box=atrial refractory event.
Figure 5B:
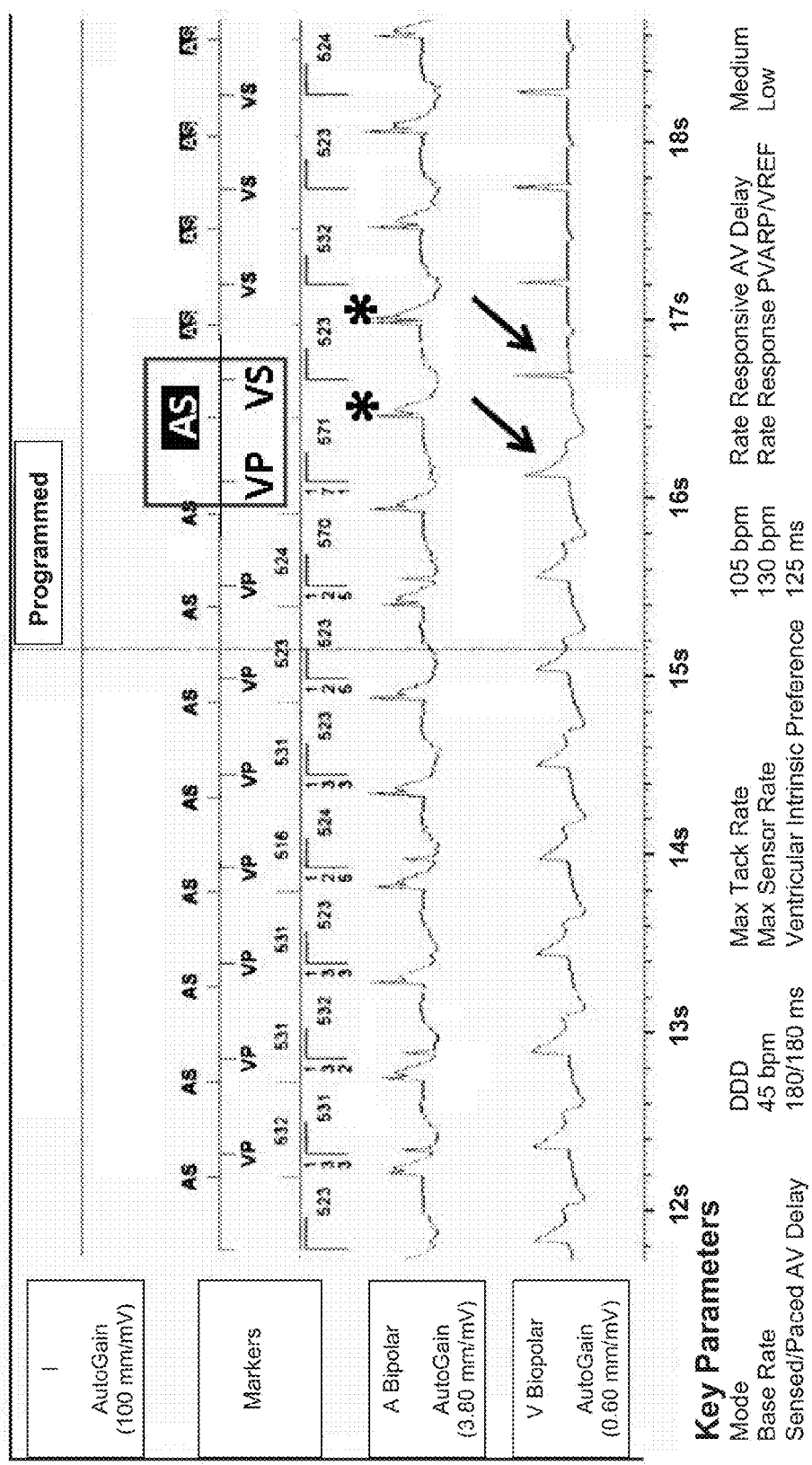
Figure 5C:
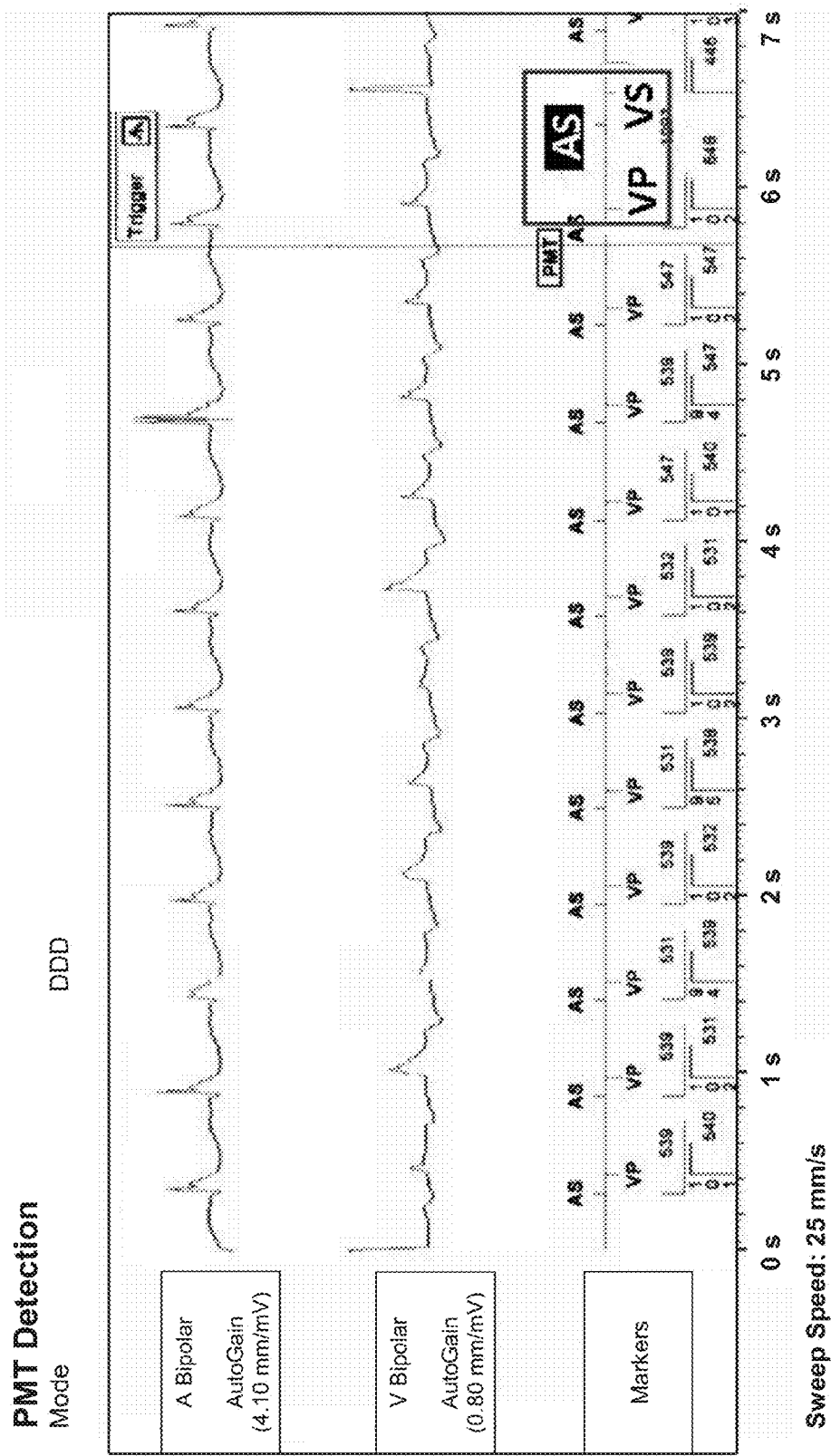

During a routine exercise treadmill test 2 months following implant, the patient developed an irregular wide complex tachycardia at a heart rate of 160 bpm, with the majority of QRS complexes being monomorphic with brief runs of polymorphic tachycardia interspersed (FIG. 4). During a follow-up exercise test, sustained monomorphic wide complex tachycardia was observed at a cycle length of approximately 530 ms and was terminated with application of a magnet over the device or with programming an extension of the PVARP from 200 to 375 ms (FIGS. 4A & B). Immediately following termination of the arrhythmia, there was also a change in morphology in the ventricular electrogram. This was consistent with the change in ventricular activation resulting from ventricular pacing during tachycardia to that of intrinsic activation during termination. In contrast, the configuration of the atrial electrogram was unperturbed, indicating that the vector of activation was identical during and after tachycardia, consistent with the diagnosis sinus/atrial tachycardia tracking. A critical finding was that the tachycardia consistently terminated with a Vp-Ar-Vs (V-A-V) response. Of note, the pacemaker's algorithm misdiagnosed this rhythm as PMT but was able to terminate the wide complex tachycardia with PVARP extension to 480 ms for a single beat, resulting in a V-A-V response (FIG. 4C).

What is claimed is:

1. A method to distinguish pacemaker-mediated tachycardia (PMT) from tracking of sinus or atrial tachycardia (AT) comprising:

analyzing, using a processor, a response to an extension of a post-ventricular atrial refractory period (PVARP), by classifying the response into responsive patterns including a V-A-V response, a V-A-A-Vs response and a V-A-A-Vp response;

determining, using the processor, a mechanism of a tachycardia based at least upon the classifying; and providing an alert of the outcome of the determining of the mechanism, wherein a mechanism of a tachycardia is determined as atrial or sinus tachycardia when the response is classified as a V-A-V response, wherein a mechanism of a tachycardia is determined as PMT when the response is classified as a V-A-A-Vs response, and wherein when the response is classified as a V-A-A-Vp response, the method further comprises:

comparing, using the processor, an atrial rate during the tachycardia and an atrial rate after the PVARP extension; and determining, using the processor, a mechanism of the tachycardia based at least upon the comparison, wherein a mechanism of a tachycardia is determined as PMT when a slower atrial rate after the PVARP extension is observed based on the comparing.

2. The method of claim 1, wherein when the response is classified as a V-A-A-Vp response and based upon the comparing, atrial electrogram morphology is used to distinguish PMT from atrial tracking.

3. The method of claim 1, wherein when the response is classified as a V-A-A-Vp response, and based upon the comparing, surface P wave morphology is used to distinguish PMT from atrial tracking.

4. The method of claim 2, wherein a mechanism of a tachycardia is determined as PMT when a change in the atrial electrogram morphology is observed.

5. The method of claim 3, wherein a mechanism of a tachycardia is determined as PMT when a change in the surface P wave morphology is observed.

6. The method of claim 1, wherein the processor is included in a cardiac pacemaker.

7. A method to correct pacemaker facilitated tachycardia comprising:

performing the method of claim 1, wherein if the determined mechanism is PMT, at least one control parameter of the cardiac pacemaker is adjusted.

8. A method to correct pacemaker facilitated tachycardia comprising:

performing the method of claim 1, wherein if the determined mechanism is AT, at least one treatment parameter of a patient is adjusted.

9. The method to correct pacemaker facilitated tachycardia according to claim 8, wherein the at least one treatment parameter is selected from a group consisting of: medications, ablation procedure and intervention with anti-tachycardia pacing/cardioversion.

10. The method of claim 1, wherein the processor is included in an implantable cardioverter-defibrillator.

11. A chronic implantable electronic device (CIED) comprising:

a storage device configured to store a computer readable program, a processor, configured to, when executing the computer readable program provide:

an analyzing unit configured to analyze a response to an extension of a post ventricular atrial refractory period (PVARP), by classifying the response into responsive patterns including a V-A-V response, a V-A-A-Vs response and a V-A-A-Vp response;

a determining unit configured to determine a mechanism of a tachycardia based at least upon the classifying, wherein a mechanism of a tachycardia is determined as atrial or sinus tachycardia when the response is classified as a V-A-V response and wherein a mechanism of a tachycardia is determined as pacemaker-mediated tachycardia (PMT) when the response is classified as a V-A-A-Vs response; and a comparing unit configured to compare an atrial rate during the tachycardia and an atrial rate after the PVARP extension, wherein when the response is classified as a V-A-A-Vp response, the determining unit is further configured to also use a result of the comparing to determine a mechanism of the tachycardia, a mechanism of a tachycardia is determined as PMT when a slower atrial rate after the PVARP extension is observed based on the comparing, wherein the processor further configured to, when executing the computer readable program, adjust at least one control parameter of the CIED when the determined mechanism is PMT.

12. The CIED of claim 11, wherein the storage device is further configured to store a correspondence between the responsive patterns and mechanisms of the tachycardia.

13. The CIED of claim 11, further comprising a transmitting unit configured to provide an alert of the outcome of the determining of the mechanism.

14. The CIED of claim 11, wherein the CIED is a cardiac pacemaker.

15. The CIED of claim 11, wherein the CIED is an implantable cardioverter-defibrillator (ICD).

16. The CIED of claim 11, wherein the adjusting is automatic.

17. A chronic implantable electronic device (CIED) comprising:

a storage device configured to store a computer readable program, a processor, configured to, when executing the computer readable program provide:

an analyzing unit configured to analyze a response to an extension of a post ventricular atrial refractory period (PVARP), by classifying the response into responsive patterns including a V-A-V response, a V-A-A-Vs response and a V-A-A-Vp response;

a determining unit configured to determine a mechanism of a tachycardia based at least upon the classifying, wherein a mechanism of a tachycardia is determined as atrial or sinus tachycardia when the response is classified as a V-A-V response and wherein a mechanism of a tachycardia is determined as pacemaker-mediated tachycardia (PMT) when the response is classified as a V-A-A-Vs response;

a comparing unit configured to compare an atrial rate during the tachycardia and an atrial rate after the PVARP extension; and a transmitting unit configured to provide an alert of the outcome of the determining of the mechanism, wherein when the response is classified as a V-A-A-Vp response, the determining unit is further configured to also use a result of the comparing to determine a mechanism of the tachycardia, a mechanism of a tachycardia is determined as PMT when a slower atrial rate after the PVARP extension is observed based on the comparing.

18. The CIED of claim 17, wherein the CIED is selected from a group consisting of an implantable cardioverter-defibrillator (ICD) and a cardiac pacemaker.

19. The CIED of claim 17, wherein the storage device is further configured to store a correspondence between the responsive patterns and mechanisms of the tachycardia.

* * * * *